(12) United States Patent
Tomich et al.

(10) Patent No.: US 7,823,321 B2
(45) Date of Patent: Nov. 2, 2010

(54) DNA SAMPLING HOOK

(75) Inventors: Stan D. Tomich, Seattle, WA (US);
Marjory E. Clarke, Seattle, WA (US);
John H. Harms, Seattle, WA (US);
Jennifer A. Hempelmann, Seattle, WA (US)

(73) Assignee: The United States of America as represented by the Secretary of Commerce, Washington, DC (US)

( * ) Notice: Subject to any disclaimer, the term of this patent is extended or adjusted under 35 U.S.C. 154(b) by 300 days.

(21) Appl. No.: 12/021,091

(22) Filed: Jan. 28, 2008

(65) Prior Publication Data

US 2009/0188150 A1  Jul. 30, 2009

(51) Int. Cl.
*A01K 83/00* (2006.01)
*A01K 83/02* (2006.01)
(52) U.S. Cl. ..................... 43/43.4; 43/43.16
(58) Field of Classification Search .............. 43/43.16, 43/43.2, 43.4, 43.6, 44.82; 600/101, 184, 600/567, 108
See application file for complete search history.

(56) References Cited

U.S. PATENT DOCUMENTS

| 2,217,928 | A |   | 10/1940 | Ward ................... 43/43.16 |
|---|---|---|---|---|
| 2,815,603 | A | * | 12/1957 | Bandemer ............. 43/43.16 |
| 3,154,876 | A | * | 11/1964 | O'Neil .................. 43/37 |
| 3,397,477 | A |   | 8/1968 | Hand .................... 430/15 |
| 3,497,985 | A |   | 3/1970 | Margulies .............. 430/35 |
| 3,624,690 | A |   | 11/1971 | Ashley ................. 43/43.16 |
| 3,827,174 | A | * | 8/1974 | Banker ................. 43/43.16 |
| 3,983,655 | A |   | 10/1976 | Kolesar ................ 43/42.1 |
| 4,126,957 | A | * | 11/1978 | Randall ................ 43/43.16 |
| 4,543,742 | A | * | 10/1985 | Rand, Jr. .............. 43/43.16 |
| 4,590,700 | A | * | 5/1986 | Klein ................... 43/5 |
| 4,858,371 | A |   | 8/1989 | Preiser ................. 43/43.16 |
| 4,987,695 | A |   | 1/1991 | Preiser ................. 43/42.41 |
| 5,233,784 | A | * | 8/1993 | Ellis et al. ............ 43/37 |
| 5,363,588 | A |   | 11/1994 | Konow ................. 43/43.16 |

(Continued)

FOREIGN PATENT DOCUMENTS

AU        2002/953016        12/2002

(Continued)

*Primary Examiner*—David J Parsley
(74) *Attorney, Agent, or Firm*—Robert Platt Bell (57) ABSTRACT

The DNA Sampling Hook is a significant improvement on a method of obtaining a tissue sample from a live fish in situ from an aquatic environment. A tissue sample taken from a live fish can be used for DNA analyses, which can identify the species of fish, as well as the unique individual fish. Taking a small tissue sample without bringing the fish to the surface is important as it allows for observing the fish community without harming the individual fish by inducing barotrauma or other stresses associated with bringing a fish up from depth, which can be lethal to the animal. These tissue samples are obtained by hook and line methods and do not capture or traumatize the fish resulting in a non-lethal and non-destructive method of observing fish individuals and species. The DNA Sampling Hook is specifically designed to virtually eliminate a condition called double bites, in which more than one individual fish gives up tissue to the same hook. It is also designed to protect the tissue sample in an enclosed manner and the device can be reused repeatedly for a total overall reduction in cost for programs requiring extensive numbers of tissue samples for DNA analysis.

20 Claims, 4 Drawing Sheets

U.S. PATENT DOCUMENTS

| | | | |
|---|---|---|---|
| 5,388,367 A | 2/1995 | Rydell | 43/43.2 |
| 5,491,925 A | 2/1996 | Carpenter | 43/37 |
| 5,611,166 A | 3/1997 | Day | 43/35 |
| 5,685,108 A | 11/1997 | Lepage | 43/43.16 |
| 5,884,428 A | 3/1999 | Shelton | 43/4.5 |
| 5,946,846 A | 9/1999 | Cotton | 43/36 |
| 6,574,908 B1 | 6/2003 | Sanner | 43/36 |
| 6,739,085 B1 * | 5/2004 | Burczynski | 43/43.16 |
| 6,840,002 B1 | 1/2005 | Dick | 43/53.5 |
| 2006/0106324 A1 | 5/2006 | Buckworth | 600/567 |
| 2008/0051802 A1 * | 2/2008 | Schostek et al. | 606/108 |

FOREIGN PATENT DOCUMENTS

| | | |
|---|---|---|
| WO | WO2004/049953 | 6/2004 |
| WO | WO2006/069053 | 6/2006 |

* cited by examiner

DNA SAMPLING HOOK

STATEMENT OF GOVERNMENT INTEREST

The research that led to the development of the present invention was sponsored by the National Oceanic and Atmospheric Administration's (NOAA's) National Marine Fisheries Service (NMFS). NOAA is a part of the U.S. Department of Commerce, a component of the U.S. Federal government. The United States Government has certain rights in this invention.

FIELD OF THE INVENTION

The present invention relates to an improved DNA sampling hook for obtaining tissue samples from fish underwater, without bringing the fish to the surface.

BACKGROUND OF THE INVENTION

Sampling of fish DNA is useful to marine biologists for a number of reasons. Such samples may be used to determine the types of fish within a fishery, the genetic diversity and structure of fish populations, the historical and present size of fish populations, assess fish population growth, determine migration patterns and barriers to fish and larval dispersal, detect the presence of genetic defects, and also determine the health of the fish population. Prior Art techniques of catching fish to obtain DNA samples are expensive and time consuming, as they require that the fish be caught, brought to the surface, a DNA sample taken, and then the fish released. In many instances the fish is severely injured or dies as a result. Thus a technique for obtaining a DNA sample from a fish without having to catch and release the fish is desirable.

Fish biopsy devices are known in the art. One such device presently on the market is known as the Fish Biopsy Device. The Northwest Fisheries Science Center (NWFSC) has used the Fish Biopsy Device in prior studies in the summers of 2004 and 2005. This device, as designed, was used 1331 times and yielded 54% tissue samples, which produced usable DNA for identification of fish individuals and species. During its use, the exposed tip of the Fish Biopsy Device allowed for double bites in up to 52% of these tissue samples. The double bites then reduced the overall effectiveness of the identification from 54% collected samples to 26% for individuals and species. It was determined that the 26% identification was too low and that this number had to be improved. Additionally, the tip of the Fish Biopsy Device is difficult to replace and subsequently is just cut off from the main body for tissue analysis rendering the device unusable thereafter. This results in an overall higher cost to the projects, which require hundreds of hooks to perform scientific studies.

Published U.S. Patent Application No. 2006/0106324A1, (Buckworth), incorporated herein by reference, discloses a fish biopsy device for obtaining biopsy material in situ, which comprises a hook(s) having a tip with a tube of non-pliable material having a sharpened edge, a bend, and a shank. The device appears to suffer from the same problems as the Fish Biopsy Device mentioned above, namely the same problems (i.e., double bite, retention of samples). The reference has also been filed as PCT WO 2004/049953 based upon a 2002 Australian Patent Application.

Fishhooks and fishing gear are well known in the art as well. The following references describe Prior Art fishing gear. U.S. Pat. No. 4,858,371, (Preiser), incorporated herein by reference, discloses a retractable barb-less fishhook for sport fishing, which has an end of a bend segment carrying sharpened point and other end linked slidably movable flexible shank. This reference is directed toward a fish catching device and is relevant as background only. Note, U.S. Pat. No. 4,768,304, also incorporated herein by reference, is a family member.

U.S. Pat. No. 5,363,588, (Konow), incorporated herein by reference, discloses a hook for fishing line which has smooth hook portion with cavity adjacent point and shank with line coupling. This reference is directed toward a fish catching device and is relevant as background only.

U.S. Pat. No. 6,840,002, (Dick), incorporated herein by reference, discloses a de-hooking device for removing hook from fish or turtle's mouth, which has slidable bite sleeve capable of abutting surface of handle when positioned at one end of rod and abutting hook removal end when positioned at opposite end of rod. This reference is directed toward a fish catching device and is relevant as background only.

U.S. Pat. No. 4,987,695, (Preiser), incorporated herein by reference, discloses a retractable barb-less fishing lure, which comprises a body having front and rear end, and also having longitudinal channel through body between front and rear ends. This reference is directed toward a fish catching device and is relevant as background only.

U.S. Pat. No. 3,624,690, (Ashley), incorporated herein by reference, discloses a fishhook with retractable barb. A sleeve member in the form of a fishhook is slotted adjacent each of its closed ends. A spring wire member is slidably received in the sleeve and has one end formed to provide a barb retractable into the sleeve through one slotted end. The other end of the wire is looped and extends through the other slotted end of the sleeve. This reference is directed toward a fish catching device and is relevant as background only.

U.S. Pat. No. 2,217,928, (Ward), incorporated herein by reference, discloses a fishhook with retractable barb. U.S. Pat. No. 5,884,428, (Shelton), incorporated herein by reference, discloses a self-releasing fishing hook apparatus. U.S. Pat. No. 5,946,846, (Cotton), incorporated herein by reference, discloses a spring loaded fishing lure with easily removed fishhook especially for use in catch and release sport fishing. U.S. Pat. No. 3,827,174, (Banker), incorporated herein by reference, discloses a fishing hook openable to release fish, which has pivoted hook releasably held by movable sleeve. U.S. Pat. No. 5,388,367, (Rydell), incorporated herein by reference, discloses a fishing lure having hook(s) with sheathguard, which comprises a coil spring, fixed at one end to lure, and acting as deflective guard during fishing.

U.S. Pat. No. 5,685,108, (Lepage), incorporated herein by reference, discloses a fishhook with catch-and-release characteristics—has two depressions with sharp leading edges in the wire of the hook. U.S. Pat. No. 5,491,925, (Carpenter, R. Carter), incorporated herein by reference, discloses a device for catching fish, which has a housing formed from first and second halves, with halves including port and longitudinally extending trough for receipt of leader. U.S. Pat. No. 3,397,477, (Hand), incorporated herein by reference, discloses a fishhook with a spring and pivoting mechanism. U.S. Pat. No. 3,497,985, (Margulies), incorporated herein by reference, discloses a fishing lure with retractable hook.

U.S. Pat. No. 3,983,655, (Kolesar), incorporated herein by reference, discloses a weed resistant spinning fishing lure, which has a hook spun by a spring covered by sleeve part of rubber body resisting weeds. U.S. Pat. No. 5,611,166, (Day), incorporated herein by reference, discloses a fishing lure apparatus which has a hook assembly and trigger assembly which includes fish-strike receiving portion and an unlocking portion which releases shaft assembly from locked position. U.S. Pat. No. 6,574,908, (Sanner), incorporated herein by reference, discloses a fishing lure for catching fish, which has fishing hooks each having one end secured to a spring-loaded plunger held in hook retracted position by trigger which is activated when fish bites on lure. U.S. Pat. No. 4,543,742, (Rand, Jr.), incorporated herein by reference, discloses an anesthetic or antiseptic injecting fishhook which has a U-shaped body with tubular well and sealable chamber for holding charge of liquid.

Published PCT Application No. WO06069053, (Skiffington), incorporated herein by reference, discloses a test device and method for detection of sample analytes in which after sampling has occurred a closure is provided. Such a test device and method can be usefully employed to detect a variety of analytes including microorganisms. This reference appears to be relevant as background only as a sample-collecting device.

SUMMARY OF THE INVENTION

The present invention comprises an improved DNA Sampling Hook for obtaining a tissue sample from a live fish in situ from an aquatic environment. A tissue sample taken from a live fish can be used for DNA analyses, which can identify the species of fish, as well as the unique individual fish. Taking a small tissue sample without bringing the fish to the surface is important as it allows for observing the fish community without destroying the individual fish by inducing trauma or barotrauma as the fish brought up from depth, which is a very destructive method. These tissue samples are obtained by hook and line methods and do not capture or traumatize the fish resulting in a non-lethal and non-destructive method of observing fish individuals and species. The DNA Sampling Hook is specifically designed to virtually eliminate a condition called double bites, in which more than one individual fish gives up tissue to the same hook. It is also designed to protect the tissue sample in an enclosed manner and the device can be reused repeatedly for a total overall reduction in cost for programs requiring extensive numbers of tissue samples for DNA analyses. The DNA Sampling Hook offers many improvements over the Prior Art.

DNA Sampling Hook described herein is a significant improvement on an existing technology currently on the market as the Fish Biopsy Device. Because an improved Fish Biopsy Device was not available, NWFSC embarked on a development effort to design a better device with the intent of increasing the amount of tissue for DNA analyses, better protect it, and eliminate the double bite problem associated with the current technology. In addition, a design goal was to produce a device, which was reusable, which could result in a net lower cost for these types of devices. Twenty nine prototype hooks were used in a captive test of 13 fish contained in a large tank on NWFSC property and the results were encouraging with ample amounts of tissue, no double bites detected, and greater than 90% DNA obtained. It was decided that the design was worthy of a field test.

The new design was finalized and drawings were made and a small procurement was issued to a local small machine shop for fabrication of 50 reusable hook assemblies and 400 replaceable sampling tips. These parts were then used in a hook and line survey in California, the results of which are still under analysis. During this survey the older technology, the Prior Art Fish Biopsy Device, and the new design of the present invention, the DNA Sampling Hook, were used on two fishing boats during a hook and line survey in the waters off southern California. The results of this study are to be analyzed, and published in the scientific community.

DETAILED DESCRIPTION OF THE INVENTION

Figure 1:
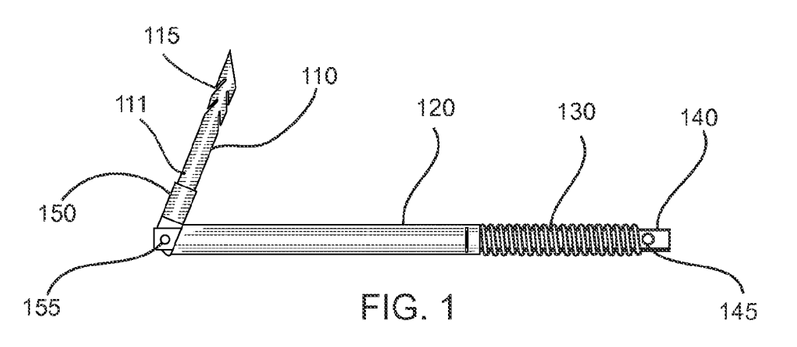
FIG. 1 is a side view of the DNA sampling hook of the present invention in the cocked position.

FIGS. 1-11 depict the DNA Sampling Hook of the present invention. FIG. 1 is a side view of the DNA sampling hook of the present invention in the cocked position. Referring to FIG. 1, the DNA sampling hook comprises a main shaft 140 provided with an eye 145 for attaching fishing line or fishing gear tackle. Attached or sliding on main shaft 140 is compression spring 130, which may be provided with a stop (not shown) to prevent it from sliding off main shaft 140, or may be held in place with a ring, clip, or the like through eye 145.

Main shaft 140 includes an attach point 145 for the line or fishing tackle, and also acts as the carrier of compression spring 130, the body on which sliding sleeve 120 may move. Main shaft 140 also includes a hinged attached point 155 for the tip holder 150. Main shaft 140 and tip holder 150 are of substantially the same diameter ensuring an easy transition route for sliding sleeve 120. Main shaft 140 may include a flat side, which the rear portion of sliding sleeve 120 is keyed (not shown) to in order to stop its forward movement at full extension of compression spring 130.

Sliding sleeve 120 slides along main shaft 140, and has a diameter slightly larger than main shaft 140 so that it may slide freely. Sliding sleeve 120 is substantially the same diameter as compression spring 130 so that one end of compression spring acts against one end of sliding sleeve 120. Hinge pin 155 allows tip holder 150 to hinge freely with main shaft 140. Replaceable tip 110 may be removably attached to tip holder 150. All of the components used may be made from Stainless Steel and adequate precision used to make the parts uniform and interchangeable. Other materials may be used, e.g., for freshwater applications, such as anodized aluminum, carbon steel, and the like. Alternately the assembly in whole or part may be made from plastic or other composite materials or the like.

Sliding sleeve 120 holds tip holder 150 to keep it at the fully cocked position and proper angle for initially hooking a fish. Sliding sleeve 120 also acts as a tissue protection sleeve, which covers replaceable tip 110, which has the fish tissue sample when the device is triggered. Compression spring 130 functions as a forcing mechanism, which holds tip holder 150 in a cocked position without the aid of a secondary device. It also is the closing mechanism to encase the tissue sample on the replaceable tip 110 with sliding sleeve 120 as tip holder 110 is rotated on hinge pin 155, allowing it to enter sliding sleeve 120 as compression spring 130 fully expands to length.

Replaceable tip 110 may comprise a hollow tube or the like, having a series of serrations to scrape tissue as shown. One end of replaceable tip 110 may be sharpened or thinned, so that when a fish bites onto the DNA sampling hook, replaceable tip 110 pierces through the fish's flesh, and a sample of flesh is retained within the tubular portion of replaceable tip 110 along with flesh caught in the serrations.

Hinge pin 155 serves as the connecting device to hold main shaft 120 and tip holder 150 together allowing tip holder 150 to rotate freely and keeping the two aligned when compression spring 130 forces sliding sleeve 120 over replaceable tip 110. Tip holder 150 serves as a mounting point and holder for replaceable tip 110 as well as the triggering point for releasing sliding sleeve 120 when it is moved sufficiently to allow it to enter sliding sleeve 120 for encasing the tissue sample.

Figure 2:
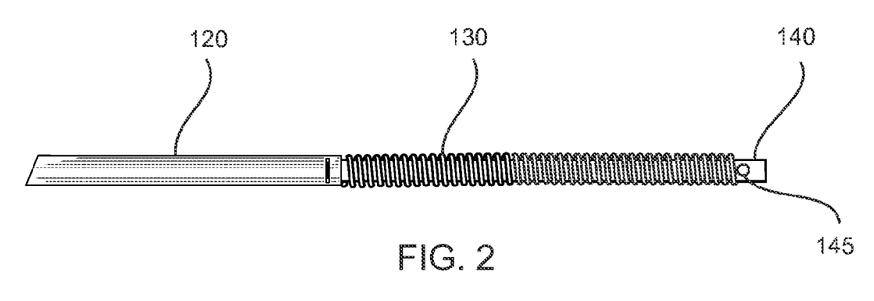
FIG. 2 is a side view of the DNA sampling hook of the present invention in the fired and covered position.

FIG. 2 is a side view of the DNA sampling hook of the present invention in the fired and covered position. As illustrated in FIG. 2, when replaceable tip 110 and tip holder 150 are rotated counter-clockwise in the picture, sleeve 120 may be driven over tip holder 150 and replaceable tip 110 by compression spring 130 so as to cover all of tip holder 150 and replaceable tip 110.

Figure 3:
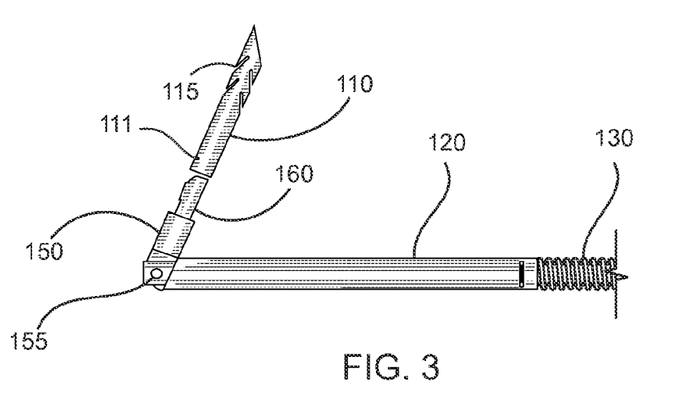
FIG. 3 is a side view of the DNA sampling hook of the present invention illustrating the removable tip, allowing re-use of the device.

FIG. 3 is a side view of the DNA sampling hook of the present invention illustrating the removable tip, allowing re-use of the device. In this Figure, replaceable tip 110 is shown removed from tip holder 150. Replaceable tip 110 may be held in place with a tab 160 which may engage a slot or groove 111 in tip 110. To remove replaceable tip 110 from tip holder 150, tab 160 may be pressed through slot 111 in removable tip 110 to allow removable tip 110 to slide off tab 160. In this preferred embodiment, a tab 160 is used, as it maintains the proper orientation of removable tip 110 to tip holder 150. However, other types of attachment mechanisms may be used, including but not limited to threaded connections, bayonet joints, adhesives, snaps, and the like.

Figure 4:
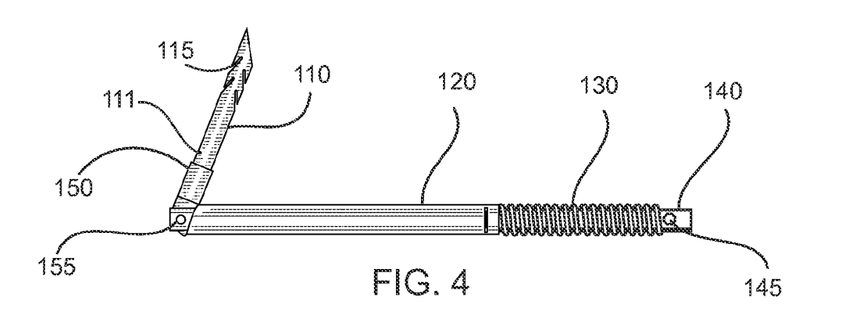
FIG. 4 is a side view of the DNA sampling hook of the present invention in position ready to bait and deploy.

FIGS. 4-8 illustrate the sequence of steps in the deployment of the DNA sampling hook of the present invention. FIG. 4 is a side view of the DNA sampling hook of the present invention in position ready to bait and deploy. In this position, the entire hook may be baited with typical fish baits. Alternately the entire assembly may be attached to an artificial lure, fly or the like. If bait is to be used, care should be taken to insure that portions of the bait are not forced into the tubular portion of replaceable tip 110. A cap or other device (not shown) may be placed over replaceable top 110 during baiting to prevent such ingress of bait flesh. Bait DNA is different and may not be a factor in locating the target fish DNA. However it is preferable to minimize the inclusion of bait flesh in the sample.

Figure 5:
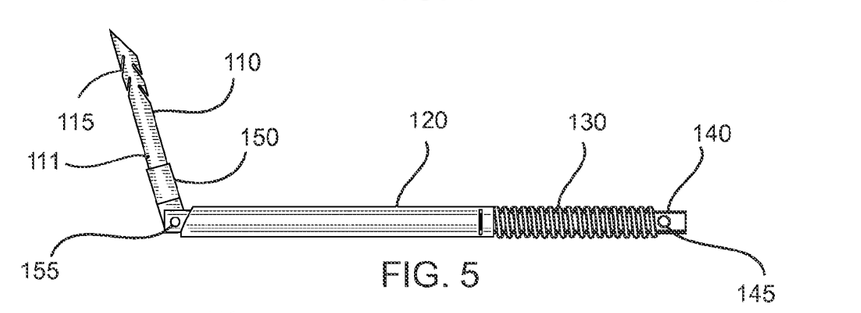
FIG. 5 is a side view of the DNA sampling hook of the present invention with the hook beginning to rotate as the fish bites.

FIG. 5 is a side view of the DNA sampling hook of the present invention with the hook beginning to rotate as the fish bites. Once baited, the DNA sampling hook of the present invention may be attached to traditional fishing gear (not shown) and lowered into the water. As with traditional fishing, fish are attracted to the bait or lure and bite down on the hook. When replaceable tip 110 pierces the flesh of the fish (e.g., jaw or the like), a portion of the fish flesh is retained within the interior of replaceable tip 110, which is tubular and hollow in construction, as well as in the serrations. The serrations may produce more tissue than the hollow area.

Figure 6:
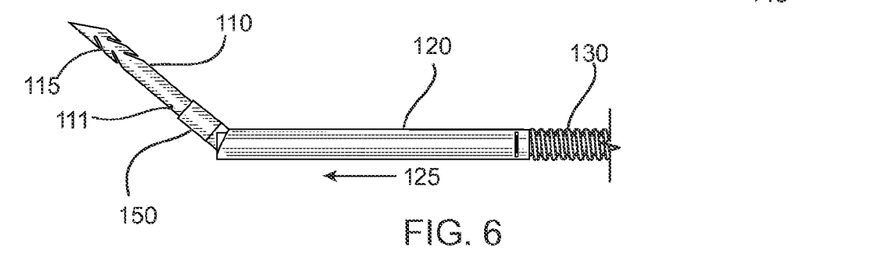
FIG. 6 is a side view of the DNA sampling hook of the present invention illustrating the compression spring-loaded sleeve pushing up the tip holder.

Once the fish bites on the hook, the user then reels in the line, or the fish will pull back from the hooked bait. In either event, as the fish pulls back from the hook, the replaceable tip 110 and tip holder 150 will rotate counterclockwise in the direction of arrow 115, as illustrated in FIG. 5. FIG. 6 is a side view of the DNA sampling hook of the present invention illustrating the compression spring-loaded sleeve pushing up the tip holder. Once replaceable tip 110 and tip holder 150 start to rotate in direction 115, sleeve 130 is no longer restrained and compression spring 130 starts to push sleeve 120 in direction 125.

Replaceable tip 110 acquires the tissue sample from the fish using built-in slots and barbs, which effectively scrape or tear tissue when encountered by the fish. Replaceable tip 110 may be preserved in the field and returned to the laboratory for tissue removal and analysis. Replaceable tip 110 may be reused if cleaned of all tissue and DNA material.

Figure 7:
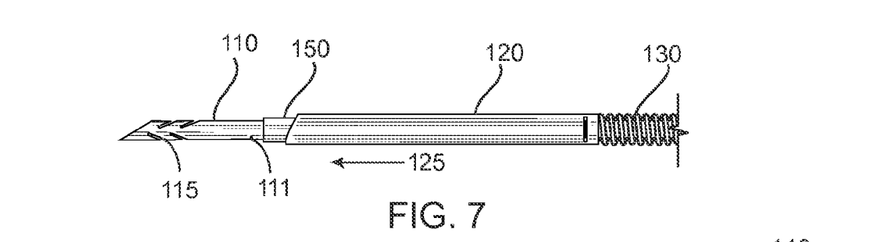
FIG. 7 is a side view of the DNA sampling hook of the present invention illustrating the sleeve continuing to push the hook tip straight.
Figure 8:
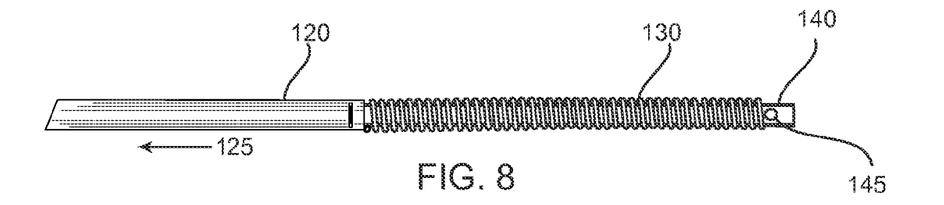
FIG. 8 is a side view of the DNA sampling hook of the present invention illustrating the completely covered top at the end of the compression spring extension.

FIG. 7 is a side view of the DNA sampling hook of the present invention illustrating the sleeve continuing to push the hoot tip straight. In FIG. 7, replaceable tip 110 and tip holder 150 are now substantially axial with main shaft 140 and sliding sleeve 120. Compression spring 130 can now push sliding sleeve 120 in direction 125 freely. FIG. 8 is a side view of the DNA sampling hook of the present invention illustrating the completely covered top at the end of the compression spring extension. Sliding sleeve 120 now completely covers replaceable tip 110 and tip holder 150 by moving in direction 125, thus protecting the fish tissue on tip 110.

This spring action acts to automatically eject the DNA sampling hook from the fish, while creating a minimum of injury to the fish, and also protecting the sample within the replaceable tip from loss or damage. In addition, since replaceable tip 110 is now protected by sliding sleeve 120, a fish cannot bite on the device again, and in addition, sliding sleeve 120 prevents other fish from biting on the device. Thus, a DNA sample is received only from the first fish to bite, and not from a plurality of fish. As the DNA sampling hook is now released from the fish, it may be reeled in to retrieve the sample.

Figure 9:
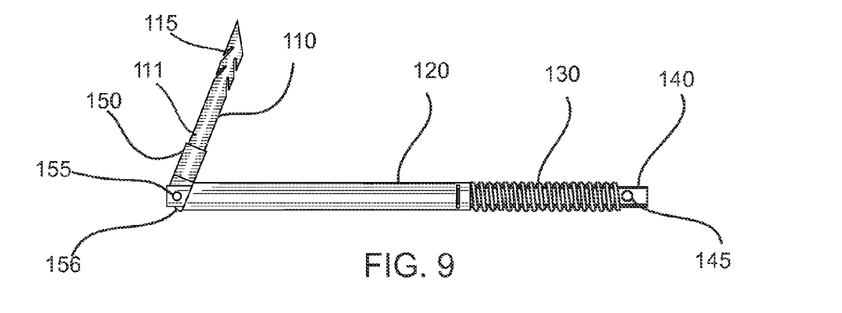
FIG. 9 is a side view of the DNA sampling hook of the present invention illustrating details of the sampling hook components.

FIG. 9 is a side view of the DNA sampling hook of the present invention illustrating details of the sampling hook components. Once retrieved (onto a boat, dock, or the like), sliding sleeve 120 may be pushed back to the position shown in FIG. 9 and replaceable tip 110 and tip holder 150 cocked back into the original position to hold sliding sleeve 120 in place. Replacable tip 110 may then be removed as illustrated in FIG. 3, and the entire tip, including sample may be tagged and stored for later analysis. A new replacement replaceable tip 110 may then be quickly attached to tip holder 150 and the process quickly repeated. Since there is no need to remove the sample from the DNA sampling hook, more sampling can occur in a given time. In addition, in a rocking boat or on a dock, it may be difficult and unsanitary to try to remove flesh samples from a Prior Art hook, catalog and store such samples. The replaceable tip of the present invention solves this problem, and also allows unskilled persons to collect such samples with less risk of contamination or the like.

Figure 10:
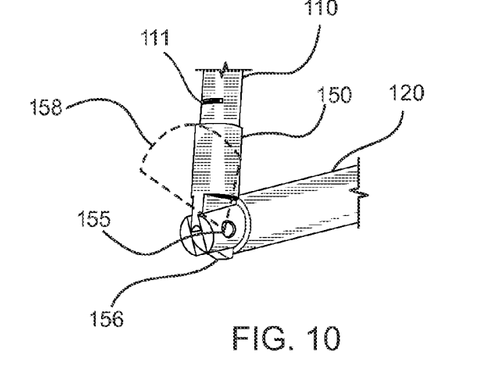
FIG. 10 is an enlarged perspective view of the DNA sampling hook of the present invention illustrating how the tip holder holds the sleeve in position prior to activation.
Figure 11:
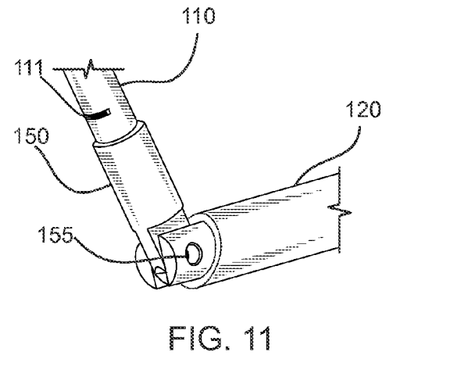
FIG. 11 is an enlarged perspective view of the DNA sampling hook of the present invention illustrating how the tip holder triggers the extension of the sleeve when a fish bites on the hook.

FIG. 10 is an enlarged perspective view of the DNA sampling hook of the present invention illustrating how the tip holder holds the sleeve in position prior to activation. FIG. 11 is an enlarged perspective view of the DNA sampling hook of the present invention illustrating how the tip holder triggers the extension of the sleeve when a fish bites on the hook. As illustrated in FIG. 10, tip holder 150 is provided with a hinge pin 155 which hinges tip holder 150 to main shaft 140. A tab 156 is provided on tip holder 150 such that it extends through a portion of main shaft 140 and acts as a stop to hold sliding sleeve 120 in place.

Once tip holder 150 rotates through a 40 degree range of motion 158, tab 156 no longer locks sliding sleeve 120 in place, and sliding sleeve, pushed by compression spring 130 may then act upon tip holder 150 to move tip holder 150 as illustrated in FIGS. 4-8. Note in this example, a 40 degree range of motion 158 is illustrated in the preferred embodiment, however other suitable angles may be used within the spirit and scope of the present invention.

The DNA Sampling Hook as some distinct and important differences from the Fish Biopsy Device. They are depicted in the following table:

TABLE 1

| DNA Sampling Hook | Fish Biopsy Device |
| --- | --- |
| Reusable design of major components including reuse of the sampling tip | Disposable device, the sampling tip is unscrewed or cut off rendering the device unusable |
| Eliminates or nearly eliminates double bites | Cannot prevent double bites |
| Encloses tissue sample to protect it from being washed away or eaten by smaller animals | Exposed tissue sample with no protection from water column or small animals |
| Mechanical action releases fish automatically after triggering | Body must be bent to release fish, device has brought fish to the surface resulting in fatalities |
| Ample amounts of tissue collected for good DNA analysis | Trace amounts of tissue collected for minimal DNA analysis |
| Positive snap action preferred for one time scientific sampling | No positive action, scientific sampling is not assured |

Applications for the DNA Sampling Hook are widespread and because the design protects the tissue sample it can be used in more scientific studies than prior art. The Fish Biopsy Device for example is used typically on hook-and-line research where the principal investigator or fisherman is involved in actively setting the hook into the fish and then retrieving it immediately to retrieve the tip and tissue sample.

The DNA Sampling Hook on the other hand, can be left in situ, because the sleeve protects the tissue sample. This tissue protection will allow the hook to be used in long line surveys where lines with hundreds of hooks are deployed and then later retrieved. Other applications include the deployment and retrieval of the DNA Sampling Hooks on robotic devices to various locations in aquatic environments not reachable by current hook and line methods. While disclosed for use with fish, the DNA sampling hook may be used also for other types of marine animals, amphibians, reptiles, land animals, mammals, and even plants.

Figures 12, 13:
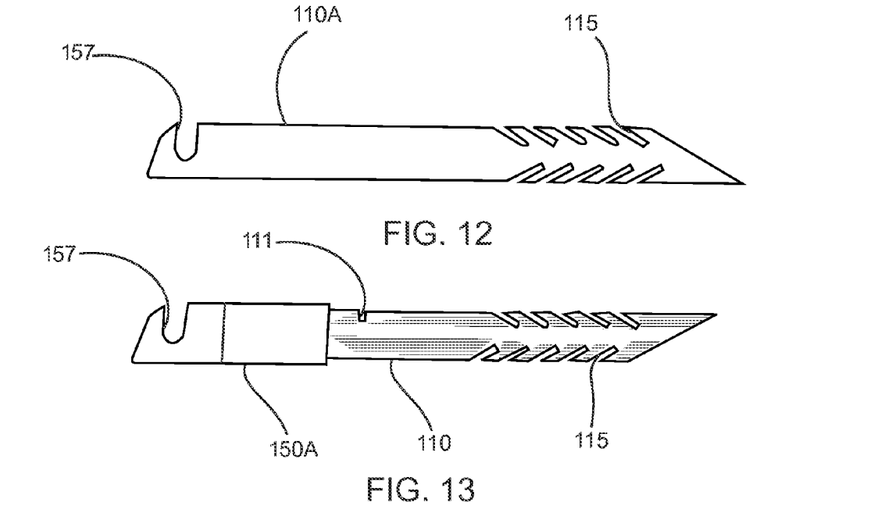
FIG. 12 is a side view of an alternative embodiment of a flat one-piece sampling hook portion with a slot attachment.
FIG. 13 is a side view of an another alternative embodiment of a sampling hook holder with a slot attachment and removable sampling hook.
Figures 14, 15:
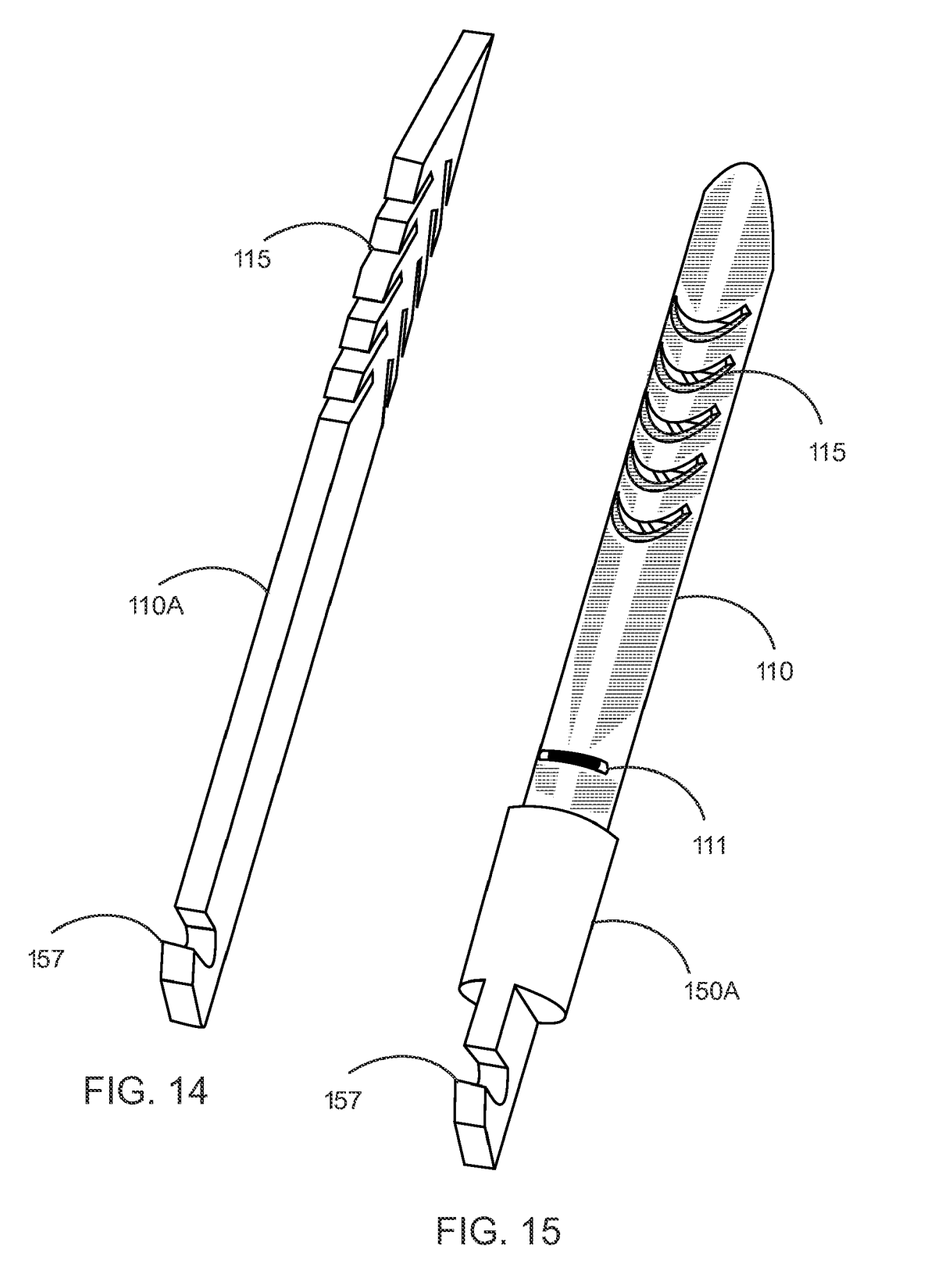
FIG. 14 is a perspective view of the flat one-piece sampling hook portion with a slot attachment of FIG. 12.
FIG. 15 is a perspective view of the sampling hook holder of FIG. 13 with a slot attachment and removable sampling hook.

FIG. 12 is a side view of an alternative embodiment of a flat one-piece sampling hook portion with a slot attachment. FIG. 14 is a perspective view of the flat one-piece sampling hook portion with a slot attachment of FIG. 12. In this embodiment, the tip holder and barbed top are combined into one single-piece tip 110A. Single piece tip 110A may be made from flat stock and may be solid, as opposed to hollow and cylindrical as in previous embodiments. Alternatively, single-piece tip 110A may be made as a hollow rectangle or the like to capture tissue samples. In yet another alternative, single-piece tip 110A may be made of round cross-section tubing as in prior embodiments, flattened at one end to form an attachment point.

Single piece tip 110A may have a flat portion at least one end with a slot 157 for attachment to the main shaft 120 as in Prior Figures. Slot 157 slides onto pivot 155 and allows the entire single piece tip 110A to be removable by sliding off one-piece tip from main shaft 120 via slot 157. Barbs 115 are provided at the other end of single piece tip 110A to capture tissue samples between barbs 115. In the preferred embodiment, single-piece tip 110A is made of solid stock and barbs 115 are the sole sampling element for tissue. Alternately, single-piece tip 110A may have a round or other open cross-section and may be hollow inside as in the other tips in order to capture tissue samples. The use of slot 157 allows for easy removal and replacement and is lower in cost that other designs, as the number of parts is reduced.

FIG. 13 is a side view of an another alternative embodiment of a sampling hook holder with a slot attachment and removable sampling hook. FIG. 15 is a perspective view of the sampling hook holder of FIG. 13 with a slot attachment and removable sampling hook. In this embodiment, round tip 110 and holder 150A are essentially the same as in prior embodiments, except that holder 150A contains slot 157 for easy removal and replacement.

The overall size of the invention may be altered depending upon which size fish (or animal or plant) is to be sampled. The overall hook size may be scaled up or down to match the size of the target fish or other sample target. As may be appreciated from the foregoing description, the sampling hook of the present invention better protects the sample during the handling on the boat, transfer to the lab, and handling in the lab. Prior art sampling devices were more subject to contamination or loss of tissue.

While the preferred embodiment and various alternative embodiments of the invention have been disclosed and described in detail herein, it may be apparent to those skilled in the art that various changes in form and detail may be made therein without departing from the spirit and scope thereof.

For example, the sampling hook of the present invention may be used be used in Robotic applications such as manned and unmanned vehicles, ROVs, AUVs, tethered or free-floating Buoys, use by Scuba divers. While the present invention has been used in a saltwater environment, the sampling hook of the present invention may be applied to freshwater applications, such as estuaries, lakes, ponds, and the like. The sampling hook may also be used in tanks and closed environments. As previously noted, the sampling hook may be used for biting animals other than fish, such as amphibians or the like, or may even be used to snag samples from non-biting animals or even plants.

We claim:

1. A sampling device comprising:
   a linear main shaft having a main axis and having a first end with an attachment point for attaching to a line and a second end with a pivot;
   a linear sampling tip, having one end pivotally coupled to the pivot on the second end of the main shaft, and an other end retrieving a sample tissue;
   a linear sliding sleeve, having a diameter larger than the main shaft and the linear sampling tip and located on the main axis and around the main shaft and sliding on the main shaft; and
   a spring, having a diameter larger than the main shaft and substantially the same diameter of the sliding sleeve and located on the main axis and around the main shaft between the attachment point and the pivot, and sliding on the linear main shaft and in contact with the sliding sleeve,
   wherein when the linear sampling tip is in a first location pivoted away from the axis of the main shaft, the sliding sleeve is held against the spring in tension at one end of the sliding sleeve and the sliding sleeve is held against a side portion of the linear sampling tip when the linear sampling tip is in a first location pivoted away from the axis of the linear main shaft such that the sampling device forms a hook, and
   wherein when pressure is applied against the linear sampling tip, the sampling tip rotates to align with the main axis of the linear main shaft and co-linear with the main shaft such that the spring pushes the sliding sleeve over the sampling tip.

2. The sampling device of claim 1, further comprising:
   a tip holder, pivotally attached to the pivot on the second end of the linear main shaft,
   wherein the linear sampling tip is removably attached to one end of the tip holder, for retrieving a sample tissue.

3. The sampling device of claim 2, wherein the tip holder is pivotally attached to the main shaft through a slot such the tip holder may be removed from the linear main shaft by disengaging the slot from the pivot.

4. The sampling device of claim 1, wherein the linear sampling tip is pivotally attached to the linear main shaft through a slot such the linear sampling tip may be removed from the linear main shaft by disengaging the slot from the pivot.

5. The sampling device of claim 1, wherein the linear sampling tip comprises a linear hollow tubular portion for receiving a tissue sample.

6. The sampling device of claim 5, wherein the linear hollow tubular portion further comprises one or more barbs for cutting into tissue.

7. The sampling device of claim 2, wherein the tip holder further includes a tab, extending from an end opposite from the one end of the tip holder where the linear sampling tip attaches, the tab extending beyond the pivot so as to engage the linear sliding sleeve when the tip holder is in the first location to hold the linear sliding sleeve in place.

8. The sampling device of claim 2, wherein the linear sampling tip comprises a slot for locking the linear sampling tip to the tip holder, the tip holder including a tab for engaging the slot to hold the linear sampling tip in place, wherein when the tab is depressed through the slot, the linear sampling tip may be removed.

9. The sampling device of claim 2, wherein the linear sampling tip is attached to the tip holder by one of a bayonet joint, a threaded joint, a clip, an adhesive, and a snap.

10. The sampling device of claim 1, wherein the linear main shaft has a stop engaging a portion of the spring to prevent the spring from sliding off the main shaft.

11. The sampling device of claim 1, wherein the linear sampling tip comprises a flat solid portion provided with barbs for receiving a tissue sample.

12. The sampling device of claim 1, wherein when the linear sampling tip is in the first position, the sampling device forms a fishhook, and when a fish bites on the fishhook, pressure is applied to the linear sampling tip to trigger the linear sampling tip into the second position, wherein pressure from the spring to the linear sliding sleeve forces the linear sampling tip into the second position as the linear sliding sleeve slides over the linear sampling tip.

13. The sampling device of claim 12, wherein when the fish bits onto the fishhook, the linear sampling tip punctures tissue of the fish, retaining a sample of the fish tissue.

14. A sampling device, comprising:
   a main shaft having a main axis and having a first end with an attachment point attaching to a line and a second end with a pivot;
   a sampling tip, having one end pivotally coupled to the main shaft, and an other end retrieving a sample tissue;
   a sliding sleeve, having a diameter larger than the main shaft and the sampling tip and located on the main axis and around the main shaft and sliding on the main shaft; and
   a spring, having a diameter larger than the main shaft and substantially the same diameter of the sliding sleeve and located on the main axis and around the main shaft between the attachment point and the pivot, and sliding on the main shaft and in contact with the sliding sleeve,
   wherein when the sampling tip is in a first location pivoted away from the axis of the main shaft, the sliding sleeve is held against the spring in tension at one end of the sliding sleeve and the sliding sleeve is held against a side portion of the sampling tip when the sampling tip is in a first location pivoted away from the axis of the main shaft such that the sampling device forms a hook, and
   wherein when pressure is applied against the sampling tip, the sampling tip rotates to align with the main axis of the main shaft such that the spring pushes the sliding sleeve over the sampling tip, and
   wherein the sampling tip is pivotally attached to the main shaft through a slot such that the sampling tip may be removed from the main shaft by disengaging the slot from the pivot.

15. The sampling device of claim 14, wherein the sampling tip comprises a hollow tubular portion for receiving a tissue sample.

16. The sampling device of claim 15, wherein the hollow tubular portion further comprises one or more barbs for cutting into tissue.

17. The sampling device of claim 14, wherein the sliding sleeve has a stop engaging a portion of the main shaft to prevent the sliding sleeve from sliding off the main shaft.

18. The sampling device of claim 14, wherein the sampling tip comprises a solid portion provided with barbs for receiving a tissue sample.

19. The sampling device of claim 14, wherein when the sampling tip is in the first position, the sampling device forms a fishhook, and when a fish bites on the fishhook, pressure is applied to the sampling tip to trigger the sampling tip into the second position, wherein pressure from the spring to the sliding sleeve forces the sampling tip into the second position as the sliding sleeve slides over the sampling tip.

20. The sampling device of claim 19, wherein when the fish bits onto the fishhook, the sampling tip punctures tissue of the fish, retaining a sample of the fish tissue.

* * * * *